(12) United States Patent
Al-Ali

(10) Patent No.: US 8,911,377 B2
(45) Date of Patent: Dec. 16, 2014

(54) PATIENT MONITOR INCLUDING MULTI-PARAMETER GRAPHICAL DISPLAY

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 1176 days.

(21) Appl. No.: 12/559,815

(22) Filed: Sep. 15, 2009

(65) Prior Publication Data

US 2010/0069725 A1 Mar. 18, 2010

Related U.S. Application Data

(60) Provisional application No. 61/097,185, filed on Sep. 15, 2008.

(51) Int. Cl.
*A61B 5/00* (2006.01)
*G06F 19/00* (2011.01)
*A61B 5/1455* (2006.01)
*A61B 5/0205* (2006.01)
*G06Q 50/00* (2012.01)

(52) U.S. Cl.
CPC ............ *A61B 5/6826* (2013.01); *A61B 5/6838* (2013.01); *G06F 19/3487* (2013.01); *G06F 19/3406* (2013.01); *A61B 5/743* (2013.01); *A61B 5/14551* (2013.01); *A61B 5/7445* (2013.01); *A61B 5/0205* (2013.01)
USPC .......................................... 600/481; 600/301

(58) Field of Classification Search
CPC ..... A61B 5/742; A61B 5/0402; G06F 19/322
USPC .................................. 600/300, 301; 705/2, 3
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,278,627 A | 1/1994 | Aoyagi et al. |
| 5,337,744 A | 8/1994 | Branigan |
| 5,341,805 A | 8/1994 | Stavridi et al. |
| 5,355,893 A | 10/1994 | Mick et al. |
| D353,195 S | 12/1994 | Savage et al. |

(Continued)

FOREIGN PATENT DOCUMENTS

WO  WO2006/033038  3/2006

OTHER PUBLICATIONS http://dictionary.reference.com/browse/graph?s=t.*

(Continued)

*Primary Examiner* — Jacqueline Cheng
*Assistant Examiner* — Puya Agahi
(74) *Attorney, Agent, or Firm* — Knobbe Martens Olson & Bear LLP

(57) ABSTRACT

A patient monitoring system and method are disclosed which provide a caregiver with more easily identifiable indications of the state of multiple physiological parameters in order to give the caregiver an indication of the patient's overall wellness in an efficient manner. Multiple physiological parameter sets are plotted on a graph, along with an indication of each parameter set's normal range. An overlapping area for all set's normal ranges provides an indication of an ideal patient state. In an embodiment, alerts are generated based on parameters distance from normal readings.

20 Claims, 11 Drawing Sheets

(56) References Cited

U.S. PATENT DOCUMENTS

| | | |
|---|---|---|
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,443,889 B1 | 9/2002 | Groth et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |

(56) References Cited

U.S. PATENT DOCUMENTS

| | | |
|---|---|---|
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |

(56) References Cited

U.S. PATENT DOCUMENTS

| | | |
|---|---|---|
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | Macneish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 2004/0127775 A1* | 7/2004 | Miyazaki et al. ............ 600/300 |
| 2004/0148140 A1 | 7/2004 | Tarassenko et al. |
| 2007/0208233 A1* | 9/2007 | Kovacs ..................... 600/300 |
| 2008/0097175 A1 | 4/2008 | Boyce et al. |
| 2008/0183054 A1* | 7/2008 | Kroeger et al. ............ 600/301 |
| 2008/0270188 A1* | 10/2008 | Garg et al. .................... 705/3 |

OTHER PUBLICATIONS

International Search Report and Written Opinion issued in Application No. PCT/US2009/057023, on Jul. 12, 2010, in 16 pages.

International Preliminary Report on Patentability in PCT/US2009/057023 dated Mar. 15, 2011 in 8 pages.

* cited by examiner

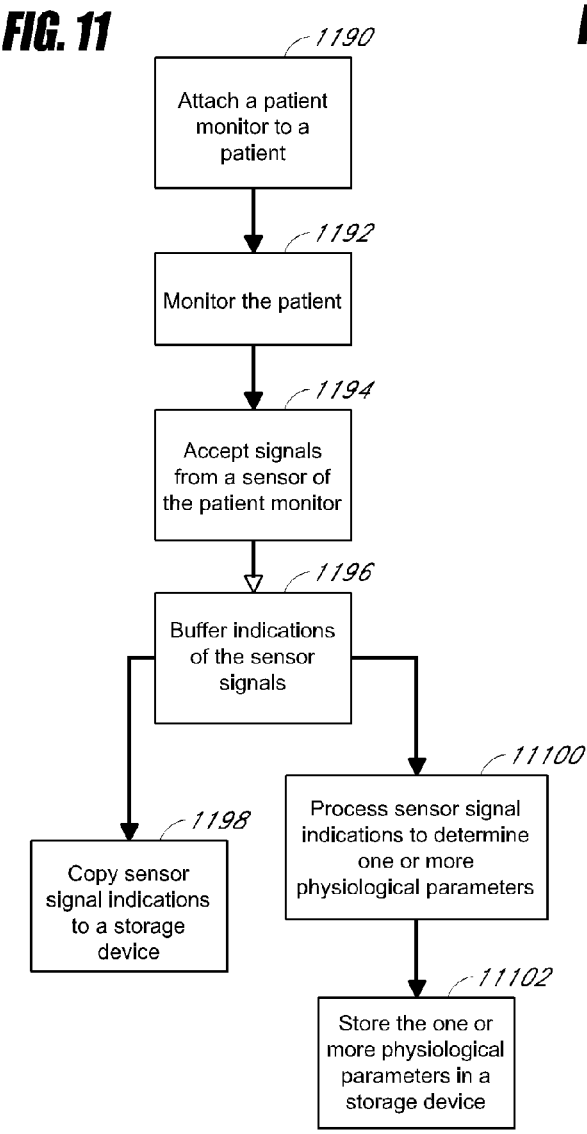
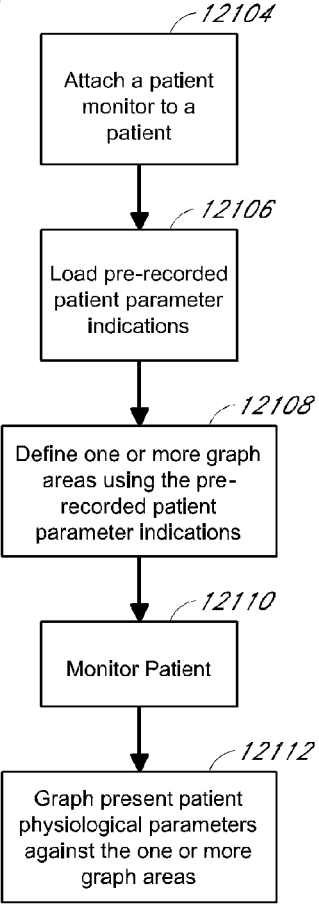

PATIENT MONITOR INCLUDING MULTI-PARAMETER GRAPHICAL DISPLAY

PRIORITY CLAIM

This application claims priority to prior U.S. Provisional Patent Application No. 61/097,185 filed Sep. 15, 2008 titled Patient Monitor Including Multi-Parameter Graphical Display, which is incorporated by reference herein.

FIELD OF THE INVENTION

The present disclosure relates to the field of patient monitors. More specifically, the disclosure relates to processing and displaying multiple parameters to quickly determine an indication of patient wellness.

BACKGROUND

In order to assess patient condition, caregivers often desire knowledge of multiple physiological parameters of the patient. These physiological parameters include, for example, oxygen saturation (SpO2), hemoglobin (Hb), blood pressure (BP), pulse rate (PR), perfusion index (PI), and Pleth Variable Index (PVI), among others. This monitoring is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents or analytes, including, for example, those listed above as well as a percent value for carbon monoxide saturation (HbCO), methemoglobin saturation (HbMet), fractional saturations, total hematocrit, billirubins, or the like. As such a pulse oximeter is one of a variety of patient monitors that help provide monitoring of a patient's physiological characteristics.

A pulse oximeter sensor generally includes one or more energy emission devices, such as specific wavelength emitting LEDs, and one or more energy detection devices. The sensor is generally attached to a measurement site such as a patient's finger, toe, ear, ankle, or the like. An attachment mechanism positions the emitters and detector proximal to the measurement site such that the emitters project energy into the tissue, blood vessels, and capillaries of the measurement site, which in turn attenuate the energy. The detector then detects that attenuated energy. The detector communicates at least one signal indicative of the detected attenuated energy to a signal processing device such as an oximeter, generally through cabling attaching the sensor to the oximeter. The oximeter generally calculates, among other things, one or more physiological parameters of the measurement site.

Pulse oximeters are available from Masimo Corporation ("Masimo") of Irvine, Calif. Moreover, some exemplary portable and other oximeters are disclosed in at least U.S. Pat. Nos. 6,770,028, 6,658,276, 6,157,850, 6,002,952, and 5,769,785, which are owned by Masimo, and are incorporated by reference herein. Such oximeters have gained rapid acceptance in a wide variety of medical applications, including surgical wards, intensive care and neonatal units, general wards, home care, physical training, and virtually all types of monitoring scenarios.

Typically, the physiological parameters are displayed to the caregiver as separate numbers on a patient monitor. Although this provides a large amount of data in a relatively small space, the greater the number of parameters being monitored, the more confusing and cluttered a display can become.

SUMMARY

A patient monitor including graphical display of combined physiological parameters provides a more powerful overall wellness assessment tool than when any physiological parameter is used by itself. A caregiver can more quickly and accurately determine if a patient is within normal parameters and which, if any, parameters may indicate a problem for the patient.

One aspect of the disclosure provides a patient monitor that can determine a range of normal, healthy parameters for a given patient and that has a display capable of providing a geometric representation of this range graphically for one or more parameters. The patient monitor can then represent whether a patient's current condition for these one or more parameters is within the normal range. In an aspect of this disclosure, the graphical presentation displays overlaying ranges for multiple parameters and provides an easy-to-understand representation of whether or not a patient is within acceptable ranges for all of the monitored parameters at once.

Another aspect of this disclosure provides that each parameter or parameter set receives a color code or codes that can be displayed when one parameter or parameter set is not within a normal range, thereby providing readily identifiable feedback to a caregiver of which monitored parameter may be a problem for the patient. Additionally, various alerts may be triggered by the monitor when one or more parameter or parameter set falls outside the normal range, including visual and/or audible alerts.

The patient parameters discussed herein also can be measured by a single device or by multiple devices that are fed into one or more patient monitoring devices in various embodiments.

In one embodiment of the present disclosure, a method for providing an indication of a patient's condition includes: noninvasively measuring a plurality of physiological parameters using a light attenuation by pulsing blood; loading a wellness range for each of two or more of the plurality of physiological parameters; displaying an area of a graph defining a normal range for the intersection of the wellness ranges of two of the plurality of physiological parameters; and plotting on the graph a point of intersection between the two physiological parameters representing a current measurement. The method can further include providing an indication that the graphed point of intersection is outside the defined normal range area, based on one or both of the graphical parameters.

In another embodiment, a method for providing an indication of a patient's condition, includes: measuring a plurality of physiological parameters; defining a first area of a graph constituting a normal range for the intersection of a first set of two of the plurality of physiological parameters; graphing a first point of intersection between the first set of two physiological parameters; defining a second area of the graph constituting a normal range for an intersection of a second set of two of the plurality of physiological parameters, wherein the second set includes at least one physiological parameter distinct from the first set; defining an intersection area of the first area and the second area; graphing a second point of intersection between the second set of two physiological parameters; and providing an indication of a state of wellness of the patient based on the first point's relation to the intersection area and second point's relation to the intersection area. The method can also indicate a state of alert when one or both of the first point and second point fall outside the intersection area. This state of alert may include an audible alert, a colored display indication, or the like.

In an embodiment, defining the second area of the graph can include normalizing the second area to increase the intersection area with the first area. In an embodiment, the first area of the graph uses data points from the physiological parameters that were gathered when the patient was known to be well. The first area may be defined by using a best fit curve analysis, may include or disregard one or more outlier points, or the like. In an embodiment, the method can further include the step of making visual representations of the first area, second area, and intersection area on a display.

In yet another embodiment of the disclosure, a system for providing an indication of a patient's condition includes: a patient monitor; a sensor for providing the patient monitor with indications of a plurality of physiological parameters; a signal processing module configured to determine values for the physiological parameters from the indications; a graphing module configured to define two or more areas of a graph, each comprising a normal range for the intersection of a set of two or more of the plurality of physiological parameters, the graphing module further configured to define an intersection area of the two or more areas; and a display configured to display a graph including the intersection area and the plurality of areas. The system can also include an alert module, capable of indicating whether a set of current sensor readings is within the intersection area of the graph. The alert module can include more than one alert level, such as to indicate various degrees of concern.

In an embodiment, the system includes a speaker, wherein the alert module sounds an alarm through the speaker if the set of current sensor readings are not within the intersection area. In yet another embodiment the patient status system includes a memory unit storing data read by the graphing module to define the area of the graph comprising the normal range for the intersection of the set of two of the plurality of physiological parameters. The memory unit stores data particular to the patient being monitored, in an embodiment, and can be removable—such as flash memory. In another embodiment, data stored on the memory unit include empirical data gathered from a plurality of individuals selected from a population.

In an embodiment, the patient status system further includes a communication module capable of connecting to a database and receiving data stored thereon for the graphing module to define the area of the graph comprising the normal range for the intersection of the set of two of the plurality of physiological parameters.

In yet another embodiment, a method for providing an individual baseline for a patient's wellness, includes the steps of: measuring a plurality of physiological parameters of the patient over a period of time, using a non-invasive sensor; identifying a plurality of graph points for the intersection of at least two of the physiological parameters, each graph point indicative of the at least two physiological parameters measured at approximately the same time; defining an area of a graph constituting a normal range from the plurality of graph points; and storing for later retrieval at least one of: (1) the plurality of physiological parameter measurements over time, (2) the plurality of graph points, or (3) the area of a graph constituting the normal range from the plurality of graph points. The method for providing an individual baseline for a patient's wellness is undertaken when the patient is healthy in some embodiments. The method for providing an individual baseline for a patient's wellness also includes loading the stored data and comparing the stored data to at least one new measurement of physiological parameters of the patient, in an embodiment, which may be done at a time when the patient's status is unknown.

BRIEF DESCRIPTION OF THE DRAWINGS

The following drawings and the associated descriptions are provided to illustrate embodiments of the present disclosure and do not limit the scope of the claims. Corresponding numerals indicate corresponding parts, and the leading digit of each numbered item indicates the first figure in which an item is found.

FIG. 11 is a block diagram of an embodiment of a method for determining a patient's healthy vital sign ranges.

FIG. 12 is a block diagram of an embodiment of a method for comparing a patient's condition to pre-recorded healthy patterns.

DETAILED DESCRIPTION

Aspects of the disclosure will now be set forth in detail with respect to the figures and various embodiments. One of skill in the art will appreciate, however, that other embodiments and configurations of the devices and methods disclosed herein will still fall within the scope of this disclosure even if not described in the detail of some other embodiments. Aspects of various embodiments discussed do not limit the scope of the disclosure herein, which is instead defined by the claims following this description.

Figure 1:
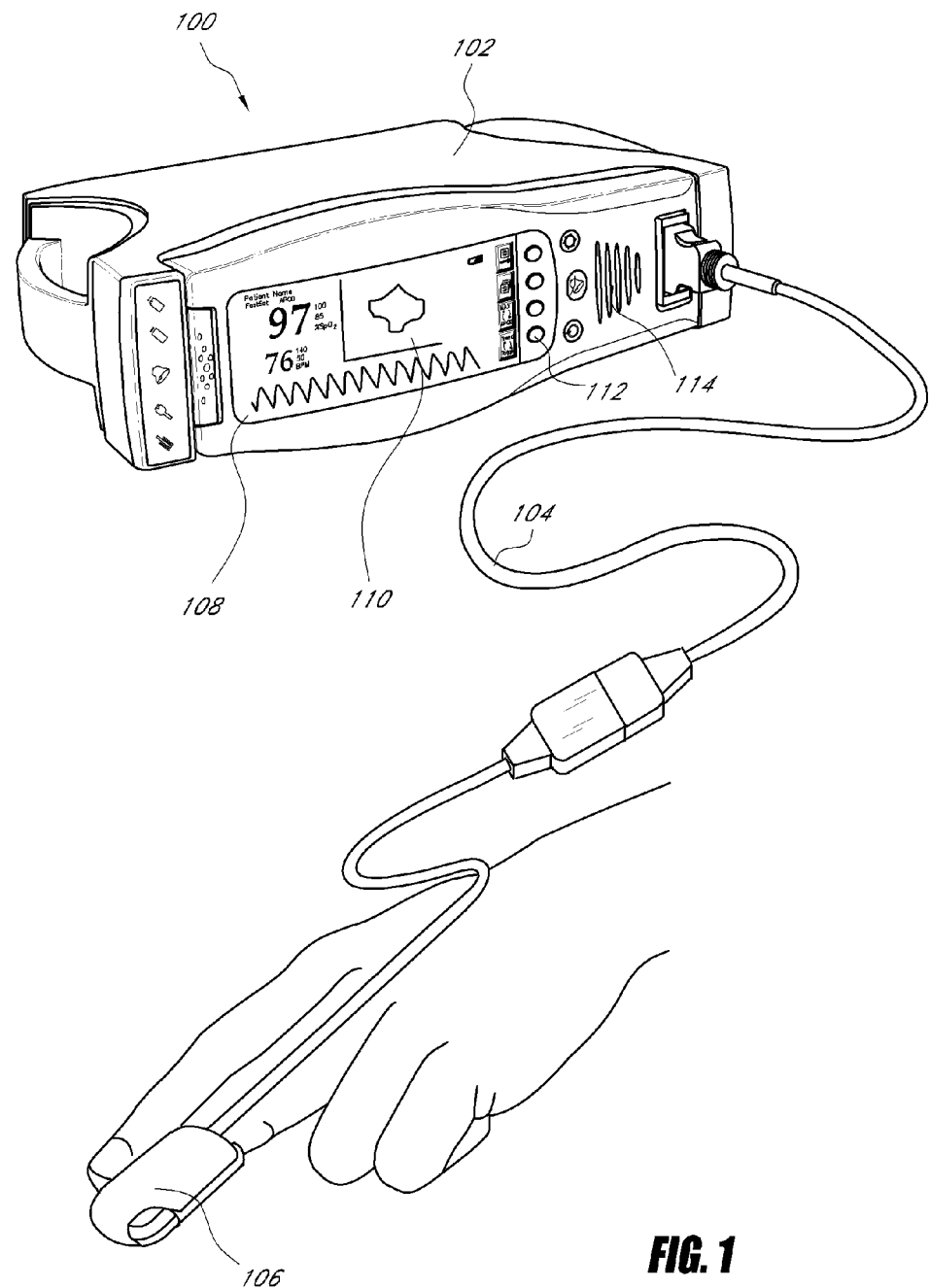
FIG. 1 illustrates a perspective view of an embodiment of a patient monitor system according to the disclosure.

Turning to FIG. 1, an embodiment of a multi-parameter patient monitor system 100 is illustrated. The patient monitor system 100 includes a patient monitor 102 attached to a sensor 106 by a cable 104. The sensor monitors various physiological data of a patient and sends signals indicative of the parameters to the patient monitor 102 for processing. The patient monitor includes a display 108 that is capable of displaying readings of various monitored patient parameters, including one or more graphs 110. Display 108 may be a liquid crystal display (LCD), a cathode ray tube (CRT), a plasma screen, a Light Emitting Diode (LED) screen, Organic Light Emitting Diode (OLED) screen, or any other suitable display. A patient monitor system 102 may monitor oxygen saturation ($SpO_2$), perfusion index (PI), pulse rate (PR), hemoglobin count, and other parameters. Typically, a patient monitor 102 will also include some sort of control interfaces 112 and a speaker 114 for audible alerts. Embodiments of a patient monitor 102 can also include inputs from other devices, such as, an EKG machine, an ECG machine, a respirator, a ventilator, a blood pressure monitor, a capnograph, combinations of the same, or the like.

Figure 2:
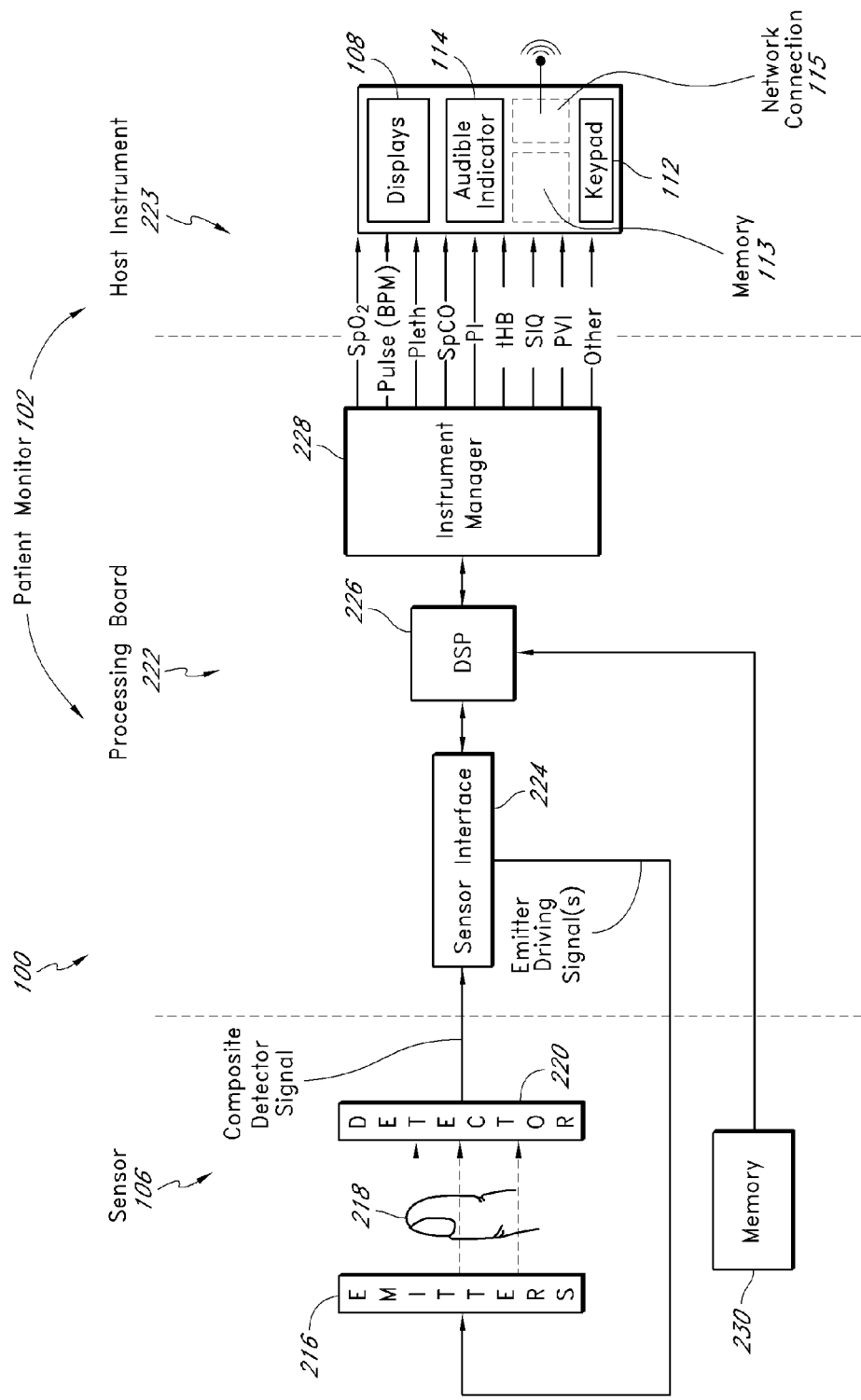
FIG. 2 illustrates a block drawing of a patient monitor system according to the disclosure.

FIG. 2 illustrates details of a patient monitor system 100 in a schematic form. Typically a sensor 106 includes energy emitters 216 located on one side of a patient monitoring site 218 and one or more detectors 220 located generally opposite. The patient monitoring site 218 is usually a patient's finger (as pictured), toe, ear lobe, or the like. Energy emitters 216, such as LEDs, emit particular wavelengths of energy through the flesh of a patient at the monitoring site 218, which attenuates the energy. The detector(s) 220 then detect the attenuated energy and send representative signals to the patient monitor 102.

Specifically, an embodiment of the patient monitor 102 includes processing board 222 and a host instrument 223. The processing board 222 includes a sensor interface 224, a digital signal processor (DSP) 226, and an instrument manager 228. The host instrument typically includes one or more displays 108, control interfaces 112, and a speaker 114 for audio messages (including alerts, tones, or verbal indicators). Control interfaces 112 may comprise buttons, a keypad, a full keyboard, a track wheel, and the like. Additionally embodiments of a patient monitor 102 can include buttons implemented in software and actuated by a mouse, trackball, touch screen, or other input device. The host instrument 223 may optionally include memory 113 and/or a wired or wireless network connection 115. Memory 113 can be used to buffer and/or store for extended periods host instrument 223 software, sensor readings, and the like. Additionally a network connection 115 may allow the host instrument 223 to communicate with other patient monitors, remote computers or displays, servers, and the like.

The signals from the sensor 106 detector(s) 220 are received by the sensor interface 224 and passed to the DSP 226 for processing into representations of physiological parameters. The sensor interface 224 may additionally perform analog and/or digital signal conditioning. These are then passed to the instrument manager 228, which may further process the parameters for display by the host instrument 223. In some embodiments, the DSP 226 also communicates with a memory 230 located on the sensor 106; it typically contains information related to the properties of the sensor that may be useful in processing the signals, such as, for example, emitter 216 energy wavelengths. Host instrument 223 then displays one or more of these physiological parameters according to instructions from the instrument manager 228. In an embodiment, the instrument manager includes a graph generation module that allows various parameters to be displayed by the host instrument 223 in graphical form.

One example parameter that may be graphed in this manner is the perfusion index (PI), which, in an embodiment of the disclosure, may include a ratio of the pulsatile blood flow to the nonpulsatile or static blood in peripheral tissue. Generally, PI is a measure of peripheral perfusion that can be continuously and noninvasively obtained from a pulse oximeter. Another exemplary parameter is the Plethysmograph Variable Index (PVI) developed by Masimo Corporation, Irvine, Calif. In an embodiment, PVI includes a measure of the dynamic changes in the perfusion index (PI) that occur during a respiratory cycle. These parameters can be graphed against others, such as pulse rate (PR), and plotted in two-dimensional space. Similarly, these and other parameters can be used and plotted in two-, three-, or more-dimensional space on the display 108.

Figure 3:
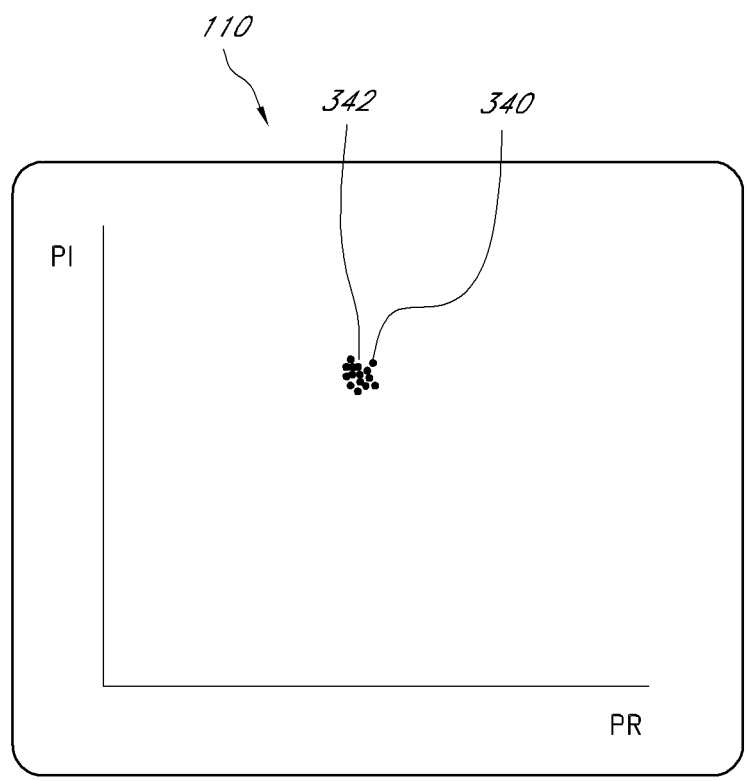
FIG. 3 illustrates an example graph that may calculated by the patient monitor system 100 of FIG. 1.

FIGS. 3-8 illustrate exemplary graphs providing disclosure of specific examples of the more general concept of multiple parameters simultaneously and graphically incorporated into a measurement and represented on display 108 of the patient monitor 102 of FIGS. 1 and 2. As shown in FIG. 3, the patient monitor 102 can display a graph plotting two physiological parameters, such as perfusion index (PI) and pulse rate (PR), versus one another. The display 108 represents a graph 110 that indicates the intersection of the respective values of PI and PR at a point in time by displaying point 340, for example. A plurality of points 342 are displayed for the intersection value of PI and PR for other points in time. The intervals between the appearances of the display points on the screen can be varied. For example, a display point 340 can be shown for readings taken every 5 seconds. A display point 340 can include a direct reading of one or more patient parameters, statistically combined measurements, corrected measurements, or the like. Further, the plurality of points 342 may show readings over a given period of time, for example, 1 hour. One or more points 340, 342 may be displayed at any given time. Displaying multiple points 342 may help provide trending data, while a single point 340 may provide the most recent measurement. In an embodiment displaying multiple points on display 108, the more recent point(s) may be displayed in a different color(s), a different shape(s), flashing, or by using some other distinguishing characteristic(s) to help differentiate it or them from previous data points.

Other combinations of physiological parameters to be displayed are possible, for example, blood pressure (BP) and perfusion index (PI) (BP/PI), blood pressure (BP) and Pleth Variable Index (PVI) (BP/PVI), Pleth Variable Index (PVI) and hemoglobin (HB) (PVI/HB), and respiratory rate (RR) and oxygen saturation ($SpO_2$). Generally, hemodynamic parameters can be compared with respiratory rate (RR) or respiratory volume (RV). Further, one of skill in the art will recognize other common parameters that may be graphed against each other to provide helpful information to a caregiver.

Figure 4:
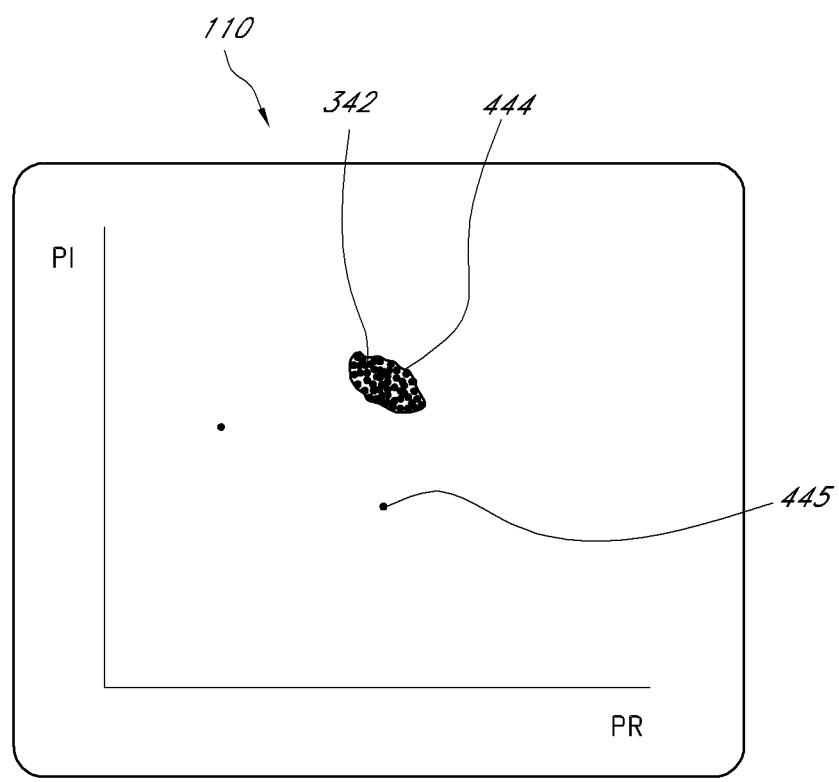
FIGS. 4-6 illustrate various examples of physiological parameter-set graphs.

Referring to FIG. 4, when a plurality of points 342 are measured—whether displayed or not—for a combination of parameters, in this case PI and PR, the scatter pattern may eventually form a cluster shape 444. As the plurality of points 342 increases, the shape 444 will generally become more defined, and an indication of the shape 444 can also be illustrated on the graph 110. The shape 444 is defined by connecting the outermost points, statistically relevant points, or the like 342, in an embodiment. In another embodiment, processing may discount one or more points 340 that are determined to be outliers 445. Similarly best fit curve processing may be used to define the shape. In an embodiment, displaying the shape 444, rather than multiple points 342, may be preferable to help avoid cluttering the graph and/or confusion with the most current reading's plotted point. In this way, a caregiver can quickly determine if the current point is within the general trending (which likely indicates a normal or at least stable condition) or outside the general trending (which may indicate a condition of concern). Similarly, movement of a current plot point away from or towards the shape 444 may indicate a degrading or improving condition, respectively.

In one use of an embodiment, when a patient is healthy or feeling normal, testing can be performed on the patient to determine patient-specific shapes 444 or at least patient-specific calibrations or normalizations of broader multi-patient shapes for combinations of various physiological parameters. Representations of these shapes 444 can then be stored with a patient record for later use. In an embodiment, the shape 444 data is stored within the patient monitor 102. In another embodiment, the data representing the shape 444 can be transferred or transmitted to another device through any of a variety of communications methods. For example, patient monitor 102 may include a wired or wireless connection to a network, such as a LAN, WAN, the Internet, or the like. Data representing the shape 444 for a patient may then be transferred to a centralized database, such as with a patient's master health records or a special purpose database for patient monitor parameters. In another embodiment, the data may be transferred to a transportable memory device, such as, for example, a disk, a CD, a DVD, a flash memory drive, a USB drive, or other memory device. This device can be provided to a patient for ready transfer among hospitals, care facilities, physician's offices, and the like. The devices can also be maintained with the patient's records for future visits. In an embodiment, for example, once a patient has been monitored while healthy for some period of time, the sensor 106 may be removed from the sensor interface 224 and a memory unit may be connected to this same port. The data in raw form of a set of data points 342 or in a processed representation of the shape 444 can be downloaded to the memory unit. It is understood that in other embodiments, the patient monitor 102 may have a separate port or drive for removable memory and/or similarly may transfer the data to a server, a database, or a computer through wired or wireless networks.

In another embodiment, a patient monitor 102 can utilize a generic shape 444 that was developed from experimental data of some number of healthy individuals. In yet another embodiment, a patient monitor 102 can begin utilizing a generic shape 444 based on empirical data and adjust the shape 444 based on the plurality of points 342 measured by monitoring the patient over time. One of skill in the art will understand that various combinations of these and similar techniques can be used for different embodiments, different sets of parameters within a single embodiment, and the like.

In an embodiment, when a patient returns for possible health reasons, the data representing the shape 444 can then be loaded into the patient monitor 102, and the patient's current readings from a patient monitor 102 can be displayed as within or external to the shape 444, indicating that the patient is within his or her normal range, borderline, abnormal, or the like. For example, if the patient's records include a flash drive that was loaded with the data representing the shape 444, the drive may first be connected to the patient monitor 102 (as at sensor interface 224 as described above), the data can be loaded, the drive removed, and finally the sensor 106 connected to the sensor interface 224 to enable patient monitoring.

In an embodiment, the patient monitor 102, through the DSP 226, the instrument manager 228, or another module—such as a particular graphical processing module, can calculate current readings and their distance from the shape 444, which may help provide an indication of the severity of a patient's condition. For example, a patient whose PI v. PR readings fall well outside the shape 444 are likely in a worse condition than those that only fall outside the shape 444 by a small amount. Additionally, trending data may be processed. For example, the greater the time that updated readings are outside the normal range, the more severe a patient's condition is likely to be. Similarly, if data indicates that parameter readings are moving away from the normal range (and thus shape 444), a patient's condition may be worsening.

Figure 5:
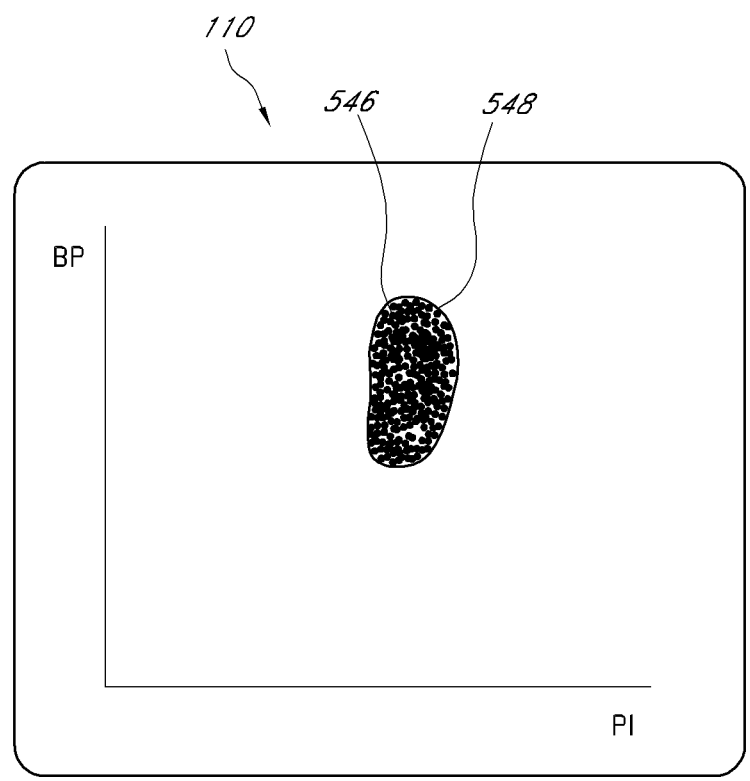
Figure 6:
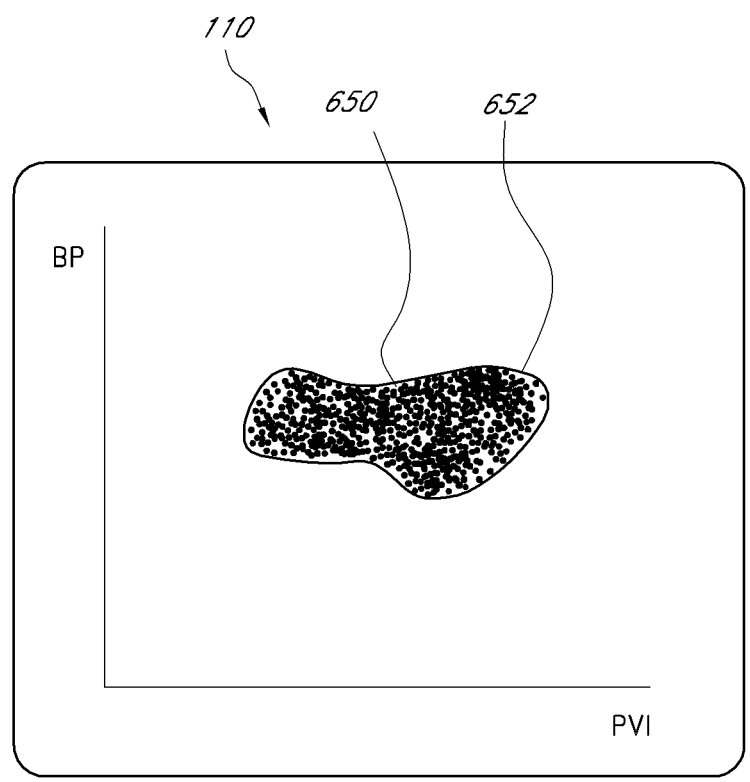
Figure 7:
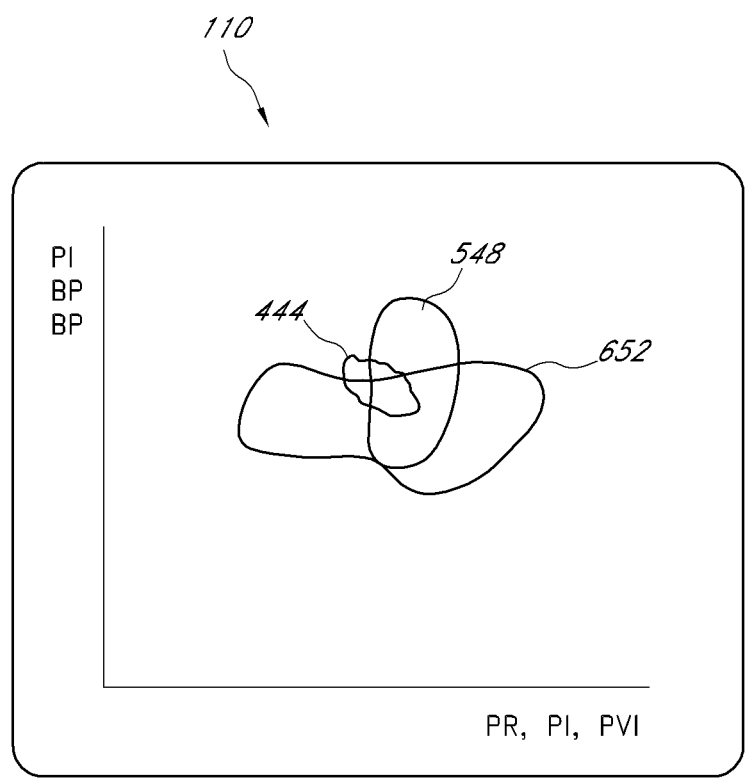
FIG. 7 illustrates an overlapping graph of FIGS. 4-6.
Figure 8:
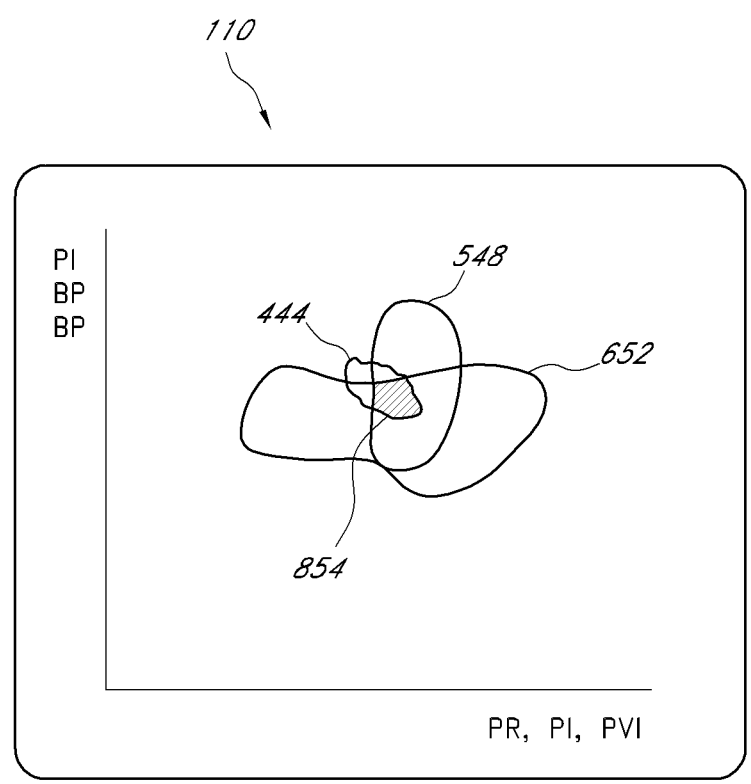
FIG. 8 illustrates the overlapping graph of FIG. 7 highlighting the area common to all three parameter-set boundaries.

FIGS. 5 and 6 illustrate other potential parameter combination examples having other shapes 548 and 652, as defined by sets of points 546 and 650, respectively. FIG. 5 represents a hypothetical shape for BP versus PI; FIG. 6 illustrates a hypothetical shape for BP versus PVI. The actual shapes 548 and 652 may be quite different, but the concepts discussed are equally applicable. These shapes 444, 548, and 652 can be considered "normal" for the patient and establish a wellness baseline for each particular combination of physiological parameters, when readings are taken while a patient is in good health. In an embodiment, these shapes 444, 548, 652 can be combined in a single graphical display (as pictured in FIG. 7). The shapes can be variously distinguished by different colors or different line or fill patterns to indicate the various combinations of elements. Additionally, as shown in FIG. 8, the combined graphs form a new shape 854 from their intersection. The intersection shape 854 defines an area where all the combinations of physiological parameters are normal for the patient and establish a combined wellness baseline. A caregiver finding all parameters within this shape can be quickly apprised that the patient is in a normal condition.

When combining these graphs to obtain an intersection shape 854, the digital signal processor 226, the instrument manager 228, or another processing unit of the patient monitor 102 may scale, shift, or otherwise normalize one or more of the various graphs to increase or maximize the overlapping areas of the multiple graphs. This would advantageously provide a greater intersection shape 854, and in turn a greater indication for caregivers of general wellness.

In contrast, if one or more of the parameters are outside the intersection shape 854, the patient monitor may trigger an alert. An alert may include a change in the display 108, such as a flashing indicator, a change in color or a highlighting of the area of the graph that is of concern, a text message on or near the graph, an increase in the size of the current plotted point, a portion of the graph, or the graph as a whole, a change in the display to the parameter or parameter set causing the alert, or the like. In an embodiment, an alert may also—or alternatively—include a tone, ring, buzz, spoken or digitally created message, or the like through the audible indicator 114. In an embodiment, alerts can change as a number of measured parameters that begin to fall outside the intersection shape 854 increases. Similarly, as measured parameters fall a greater distance from intersection shape 854, an alert may change or increase in intensity. The trending data discussed above may also affect the severity of alerts. For example, an alarm may cease or lessen if trending data indicates a reading is returning to normal.

As an example, in looking at FIG. 8, when all of the measured parameters fall within intersection shape 854, no alert is triggered. If the current measurement for PI v. PR falls outside intersection shape 854 but inside shape 444, while the other measurements remain within intersection shape 854, a first level alert may be triggered, such as a flashing of that segment of shape 444. If the same PI v. PR measurement continues to fall outside shape 444, a second level alert may be triggered, which may include both a visual indication and an audible indication. If other parameters also begin to fall outside intersection shape 854, alerts may increase to higher levels, and so on. The threshold triggers for each level of alert may differ in various embodiments, based on, for example, the particular parameters being graphically overlaid, and one of skill in the art will understand which conditions will be of greater concern.

Figure 9:
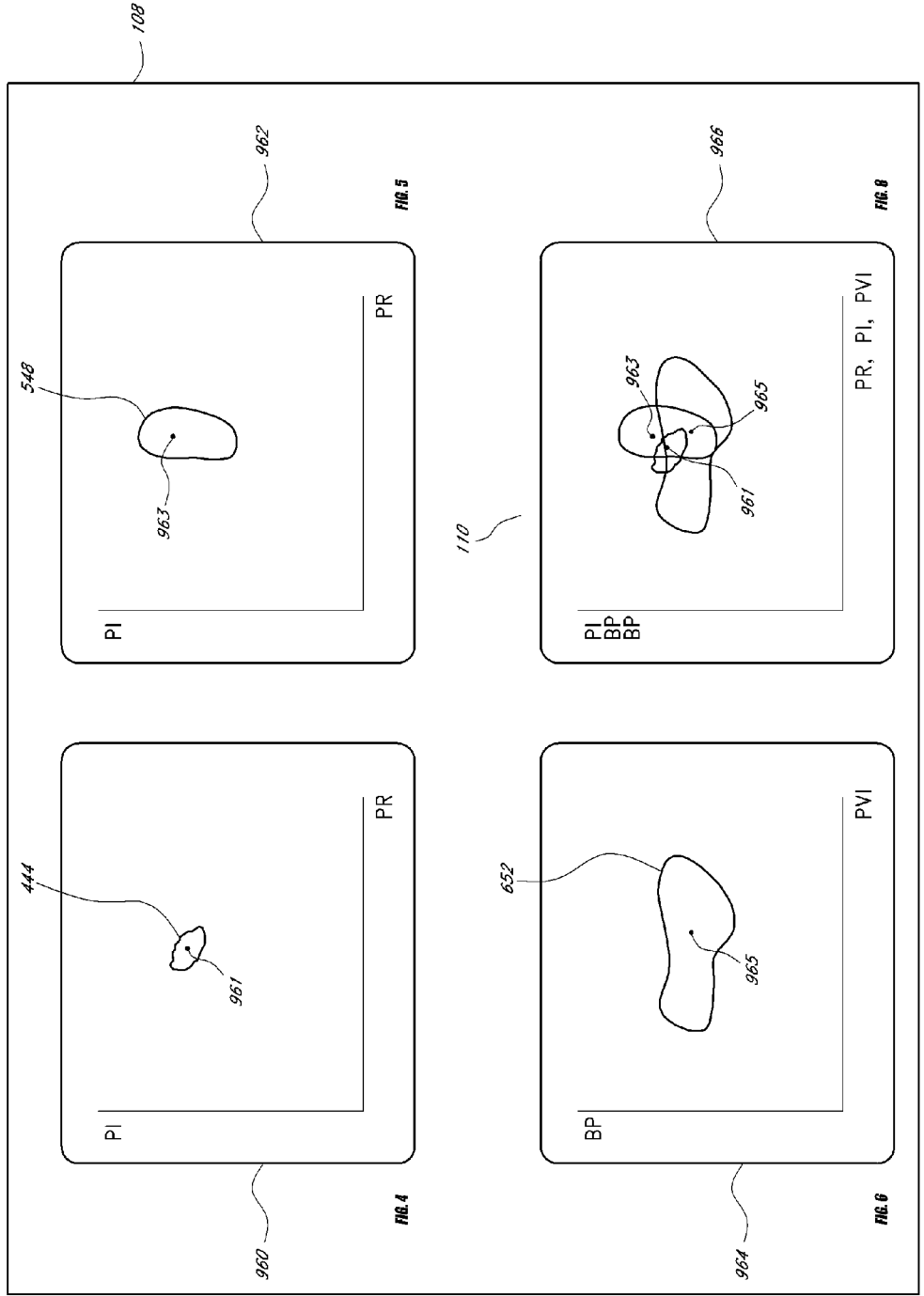
FIG. 9 illustrates an example display including both separate and combined parameter graphs.

FIG. 9 illustrates an embodiment of the layout of a display 108. In this embodiment, display 108 illustrates four graphs at the same time in different quadrants of the screen. Of course, additional data can be displayed in surrounding portions of display 108 in various embodiments as well. In the first quadrant, a graph 960 illustrates a graph similar to the PI v. PR graph of FIG. 4: shape 444 is outlined and a current reading of PI v. PR is displayed as point 961. In the second quadrant, a graph 962 illustrates a graph similar to the BP v. PI graph of FIG. 5: shape 548 is outlined and a current reading of BP v. PI is displayed as point 963. In the third quadrant, a graph 964 illustrates a graph similar to the BP v. PVI graph of FIG. 6: shape 652 is outlined and a current reading of BP v. PVI is displayed as point 965. Finally, in the fourth quadrant, graph 966 illustrates the combination of the graphs in the prior three quadrants with intersection shape 854 and the current readings points 961, 963, 965. In the example shown, both points 963 and 965 fall outside the intersection area, while point 961 is within it. This condition may trigger an alert to help highlight this state for a caregiver. However, each reading is within the normal bounds for their associated shape, so it is also possible that in an embodiment no alerts are triggered.

Figure 10:
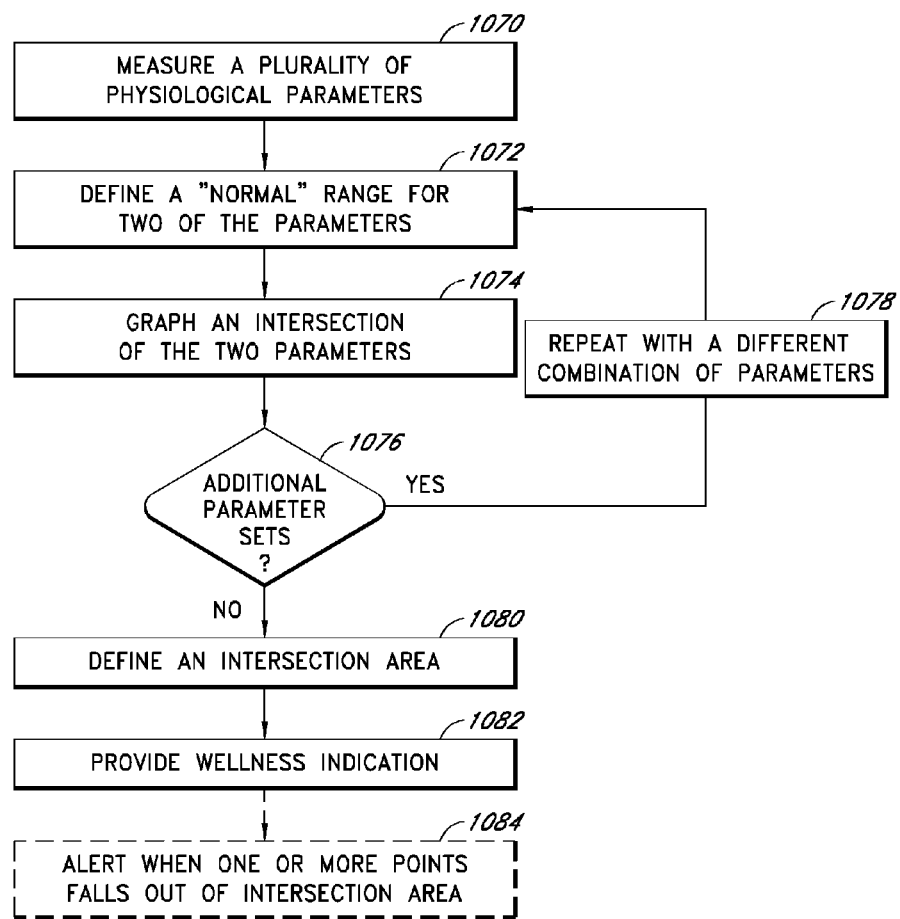
FIG. 10 is a block diagram of an embodiment of a method for indicating a patient's condition.

FIG. 10 is a block diagram illustrating one embodiment of the methods of indicating a patient's condition described herein. Starting with block 1070, a plurality of physiological parameters is measured, such as through a pulse oximeter or other patient monitor. A "normal" range is determined for the interaction of two of these physiological parameters; this range can be defined as an area of a two-dimensional graph for the intersection of the two selected physiological parameters (block 1072). As described herein, this may be determined from a set of data that was empirically gathered from a sample of the population. One alternative is to develop this from a period of measurements of the patient being monitored, once a number of parameters are measured for a period of time. In block 1074, a graph is generated of the two physiological parameters selected in block 1072. The graph may include a representation of the "normal" area and/or a point of intersection for the most recently gathered patient data. The "normal" area and/or surrounding areas can be displayed as colored areas, such as green, yellow, and red—in an embodiment—to indicate good to deteriorating conditions. In an embodiment, the graph may also display trending data, such as the most recently measured 3, 5, 10, or the like measurement points. Measurements points can be displayed as blinking or colored to help provide a more readily identifiable condition.

In block 1076, a choice is made whether to define additional parameter sets that are unique from a first pass through blocks 1072-1074. If so, then, as block 1078 indicates, two different physiological parameters are selected and blocks 1072 and 1074 are repeated. This can occur multiple times as the number of parameters sets that are desired changes. Once the desired parameter sets are defined, an intersection area consisting of the areas of the "normal" ranges that overlap for various parameter sets is defined (block 1080). In an embodiment, one or more of these parameter set graphs may be normalized to increase or maximize the intersecting area. In block 1082, the current readings for each selected parameter set are displayed in relation to the intersection area to provide an overall indication of the patient's current condition. In an embodiment, caregivers can be alerted to possible patient problems when one or more of the graphed points falls outside the intersection area (block 1084). For example, if a current reading of two parameters falls outside the intersection area, a beeping alarm may sound and/or the point may be highlighted to improve the ease of citing the potentially problematic physiological parameter.

Because each individual may have different healthy characteristics, it may prove advantageous to compare a patient's current status against the patient's own status when healthy, rather than against a generic notion of an average reading for a healthy individual. For example, it is well known that patient's may have very different resting heart rates. Many athletes, for example, have a resting heart beat that is significantly lower than even a healthy, but less active individual. As such, FIG. 11 illustrates an exemplary process for recording baseline patient physiological parameters that may allow more precise determinations of a patient's status. Starting in block 1190 in the embodiment illustrated, a patient monitoring system 100's sensor 106 is connected to a patient at a monitoring site, at block 1192 the patient is monitored, and at block 1194 detector 220 signals are accepted by the patient monitor 102 (block 1194). It is preferable that the patient undergo this monitoring during a normal scheduled check-up, or at some other time when the patient is in good health to provide the best baseline readings. As illustrated, in an embodiment, the patient monitor 102 may buffer indications of the signals from the sensor 106. These may include the signals themselves, a digital representation of them, or some other datum indicative of the signal (block 1196). In various embodiments, these indications themselves may be stored in a storage device (block 1198). As described generally above, storage devices may include a local hard drive, a networked hard drive or server, a flash drive, USB memory stick, or similar, a magnetic or optical disk, such as a CD-ROM or DVD-ROM, and the like. In one embodiment, for example, the sensor signals may be stored on a USB drive for the patient to keep for their records and stored on a server at the physician's office or uploaded to a server accessible through the Internet or the like. In an embodiment, the patient monitor communicates with such a server through a wired or wireless network connection. In another embodiment, a patient caregiver may manually upload the data to a server. Such a server may be particularly useful in that the data can then be subsequently retrieved (see discussion of FIG. 12 below) from any of a number of hospitals, urgent care facilities, physician's offices, and the like.

As an alternative, the patient monitor 102 may process the sensor signals into one or more physiological parameters before storage (blocks 11100 and 11102). In general, the signals would be processed into multiple readings of each physiological parameter over a period of time such as, for example, 10 minutes, 30 minutes, or 1 hour. Each such reading could then be stored in one or more storage devices as described above with the "raw" signal data. In yet another embodiment, the patient monitor 102 may further process the physiological parameters into the graph areas described herein and store indications of the graph areas. Such an embodiment may allow extended processing during the data gathering phase as illustrated in FIG. 11 and provide minimal data processing in the use of the data at a time when quick patient data may be critical.

The process generally described in FIG. 11 may be completed on several different occasions and two or more of the multiple sessions of sensor readings processed to determine overall physiological parameter statistics. This may further help account for normal patient condition fluctuations, changes due to an unknown illness or other medical condition, or the like.

As alluded to, FIG. 12 illustrates an embodiment of a process that utilizes stored data from a process such as that illustrated in FIG. 11. In block 12104, a patient monitor 102 sensor 106 is attached to a patient who has already completed a procedure similar to that described in FIG. 11. In block 12106, pre-recorded physiological parameter indications are loaded into memory, a cache, a buffer, or the like associated with the patient monitor 102. As described above, this data may comprise anything from raw signals from a sensor 102 to processed data representing one or more specific physiological parameter graph area indications. This data is processed (if necessary) (block 12108) for use by the patient monitor 102. Present monitoring of the patient occurs in block 12110. The patient's current status can then be displayed against the one or more graph areas for the physiological parameters of interest (block 12112). As described with respect to FIG. 10, if the current readings detected by patient monitor 102 and sensor 106 fall outside the graph area, an alert can be triggered. Although these methods are illustrated with respect to a specific embodiment having a particular order of the blocks, one of ordinary skill would understand that the arrangement of blocks is an embodiment only, and the blocks may occur in different orders or simultaneously in other embodiments without departing from the spirit of the disclosure herein.

Although the graphing of wellness indications herein is described in terms of a two dimensional graph plane, another embodiment, may combine three physiological parameters to form a three-dimensional graph. A plurality of readings of the interaction of the three physiological parameters can then define a normal volume that would correspond to the two-dimensional cluster shape 444 that is a plane. Similarly to the processes described above, multiple normal parameter volumes can be overlayed to find an intersection volume (corresponding to the intersection area 854). Displays available today are easily capable of rendering such three dimensional graphics. However, in an embodiment, a host instrument 223 rendering such graphics may further include inputs that will allow a caregiver to rotate the display around different axes. With this capability, a caregiver may more easily evaluate a situation and asses which of the different parameters may be causing an alarm state.

In other embodiments, a patient monitor system 100 automatically determines the patient parameters that can be measured from attached sensors and devices and determines one or more default graphs to generate based on those patient parameters. In another embodiment, default graphs, using default parameters, can be assigned to specific control interfaces 112, such as, for example, "hot keys," buttons, touch screen segments, combinations of the same, or the like. Additionally, alerts or alarms can include a variety of triggered actions, such as for example, sending a page to a pager, a text message, call, or voicemail to a phone, sending an email to one or more email addresses, combinations of the same, and/or the like. Alerts can also include flashing elements of the display 108, such as a graph's one or more points 342, shape 444, intersection shape 854. Beeping, tones, voice recordings or computer-generated voice messages can also be included in alerts. In an embodiment, a display 108 can be altered to display the most relevant graph to indicate out of normal parameters.

Although the foregoing has been described in terms of certain specific embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions, and modifications will be apparent to the skilled artisan in view of the disclosure herein. Thus, the present disclosure is not limited by the preferred embodiments, but is defined by reference to the appended claims. The accompanying claims and their equivalents are intended to cover forms or modifications as would fall within the scope and spirit of the disclosure.

What is claimed is:

1. A system for providing an indication of a patient's condition comprising:
    a patient monitor;
    a sensor for providing the patient monitor with indications of a plurality of physiological parameters;
    a signal processing module configured to determine values for the plurality of physiological parameters from the indications;
    a graphing module configured to define:
        a first area of a graph comprising a normal range based on a plurality of intersection points of a first physiological parameter versus a second physiological parameter,
        a second area of a graph comprising a normal range based on a plurality of intersection points of a third physiological parameter versus a fourth physiological parameter, and
        an intersection area between the first and the second area; and
    a display responsive to the graphing module to display a graph including the intersection area, the first area, and the second area.

2. The system of claim 1 further comprising an alert module, capable of indicating whether a set of current sensor readings is within the intersection area of the graph.

3. The system of claim 2 wherein the alert module includes a plurality of alert levels corresponding to increased deviation of current sensor readings from the intersection area.

4. The system of claim 2 further comprising a speaker, wherein the alert module sounds an alarm through said speaker if the set of current sensor readings are not within the intersection area.

5. The system of claim 2 further comprising a memory unit storing data read by the graphing module to define the area of the graph comprising the first area, the second area, and the intersection area.

6. The system of claim 5 wherein the memory unit stores data particular to the patient being monitored.

7. The system of claim 5 wherein the memory unit is removable.

8. The system of claim 7 wherein the memory unit comprises flash memory.

9. The system of claim 5 wherein the data stored on the memory unit comprises empirical data gathered from a plurality of individuals selected from a population.

10. The system of claim 2 further comprising a communication module capable of connecting to a database and receiving data stored thereon for the graphing module to define the area of the graph comprising the first area, the second area, and the intersection area.

11. A method of providing an indication of a patient's condition comprising:
    receiving indications from a sensor at a patient monitor of a plurality of physiological parameters;
    processing said indications with a signal processing module to determine values for the plurality of physiological parameters from the indications;
    selecting a first set of value pairs (a1, a2) from the plurality of physiological parameters, wherein a1 comprises normal range values of a first physiological parameter and a2 comprises normal range values of a second physiological parameter that is different than the first physiological parameter;
    selecting a second set of value pairs (a3, a4) from the plurality of physiological parameters, wherein a3 comprises normal range values of a third physiological parameter and a4 comprises normal range values of a fourth physiological parameter that is different than the third physiological parameter;
    displaying a first graph of the first physiological parameter versus the second physiological parameter including a first area on a display, said first area based on the first set of value pairs;
    displaying a second graph of the third physiological parameter versus the fourth physiological parameter including a second area on the display, said second area based on the second set of value pairs; and displaying a third graph including the first area, the second area and an intersection area between the first and the second area on the display.

12. The method of claim 11 further comprising indicating whether a set of current sensor readings is within the intersection area of the graph.

13. The method of claim 12 wherein said indicating includes a plurality of alert levels corresponding to increased deviation of current sensor readings from the intersection area.

14. The method of claim 12 further comprising sounding an alarm through said speaker if the set of current sensor readings are not within the intersection area.

15. The method of claim 12 further comprising storing data to define the area of the graph comprising the first area, the second area and the intersection area.

16. The method of claim 15 wherein the storing includes data particular to the patient being monitored.

17. The method of claim 15 wherein the storing occurs on a removable memory unit.

18. The method of claim 17 wherein the storing occurs on a flash memory.

19. The method of claim 15 wherein the storing includes empirical data gathered from a plurality of individuals selected from a population.

20. The method of claim 11 further comprising connecting to a database and receiving data stored thereon to define the area of the graph comprising the first area and the second area.

* * * * *